(12) United States Patent
Giambattista et al.

(10) Patent No.: US 9,795,744 B2
(45) Date of Patent: Oct. 24, 2017

(54) MEDICAMENT DELIVERY DEVICE

(71) Applicant: SHL GROUP AB, Nacka Strand (SE)

(72) Inventors: Lucio Giambattista, East Hannover, NJ (US); Antonio Bendek, Vernon, NJ (US); Dane Michael Kris, Boca Raton, FL (US)

(73) Assignee: SHL GROUP AB, Nacka Strand (SE)

( * ) Notice: Subject to any disclaimer, the term of this patent is extended or adjusted under 35 U.S.C. 154(b) by 143 days.

(21) Appl. No.: 15/014,248

(22) Filed: Feb. 3, 2016

(65) Prior Publication Data
US 2016/0151581 A1    Jun. 2, 2016

Related U.S. Application Data

(63) Continuation-in-part of application No. 14/449,671, filed on Aug. 1, 2014, now Pat. No. 9,744,307, which
(Continued)

(30) Foreign Application Priority Data

Dec. 15, 2009   (SE) ..................................... 0950958

(51) Int. Cl.
*A61M 5/00*     (2006.01)
*A61M 5/178*    (2006.01)
(Continued)

(52) U.S. Cl.
CPC ...... *A61M 5/31551* (2013.01); *A61M 5/3158* (2013.01); *A61M 5/31536* (2013.01);
(Continued)

(58) Field of Classification Search
CPC .......... A61M 5/31553; A61M 5/31561; A61M 5/3158; A61M 5/31536; A61M 5/31558;
(Continued)

(56) References Cited

U.S. PATENT DOCUMENTS 5,921,966 A *  7/1999  Bendek ................... A61M 5/24
                                                              604/207
6,042,571 A    3/2000  Hjertman et al.
(Continued)

FOREIGN PATENT DOCUMENTS

DE    102004063652    7/2006
WO    01/95959       12/2001
(Continued)

OTHER PUBLICATIONS

International Search Report and Written Opinion for International Patent App. No. PCT/US2010/060022.

*Primary Examiner* — Rebecca E Eisenberg
(74) *Attorney, Agent, or Firm* — McDonnell Boehnen Hulbert & Berghoff LLP

(57) ABSTRACT

A dose setting mechanism for a medicament delivery device is presented having a locking feature that reliably and consistently unlocks a dose injection button and concurrently a lead screw when the dose setting mechanism is transitioned from a non-activated state to an activated state. This locking feature uses dose member assembly having a rotational biasing element combined with concentric inner and outer sleeves interfacing with a locking member.

19 Claims, 12 Drawing Sheets

Related U.S. Application Data is a continuation of application No. 13/896,639, filed on May 17, 2013, now Pat. No. 8,827,962, which is a continuation of application No. 13/203,040, filed as application No. PCT/US2010/060022 on Dec. 13, 2010, now Pat. No. 8,491,536.

(51) Int. Cl.
  *A61M 5/315* (2006.01)
  *A61M 5/31* (2006.01)
  *A61M 5/24* (2006.01)

(52) U.S. Cl.
  CPC ........... *A61M 5/31553* (2013.01); *A61M 5/24* (2013.01); *A61M 5/31561* (2013.01); *A61M 2005/2407* (2013.01); *A61M 2005/3126* (2013.01); *A61M 2005/3154* (2013.01); *A61M 2205/582* (2013.01); *A61M 2205/583* (2013.01)

(58) Field of Classification Search
  CPC .. A61M 2005/3126; A61M 2005/2407; A61M 5/24; A61M 5/31551
  See application file for complete search history.

(56) References Cited

U.S. PATENT DOCUMENTS

| | | | |
|---|---|---|---|
| 6,221,053 | B1 | 4/2001 | Walters et al. |
| 2005/0165363 | A1 | 7/2005 | Judson et al. |
| 2007/0135767 | A1* | 6/2007 | Gillespie, III ...... A61M 5/2033 604/135 |
| 2008/0215001 | A1* | 9/2008 | Cowe ................... A61M 5/326 604/110 |
| 2009/0275914 | A1 | 11/2009 | Harms et al. |
| 2009/0275916 | A1 | 11/2009 | Harms et al. |
| 2011/0306947 | A1 | 12/2011 | Boyd et al. |
| 2012/0165752 | A1* | 6/2012 | Holmqvist ........ A61M 5/31553 604/211 |
| 2012/0283648 | A1 | 11/2012 | Veasey et al. |
| 2012/0302964 | A1 | 11/2012 | MacDonald et al. |

FOREIGN PATENT DOCUMENTS

| | | |
|---|---|---|
| WO | 03/080160 | 10/2003 |
| WO | 2008/101829 | 8/2008 |

\* cited by examiner

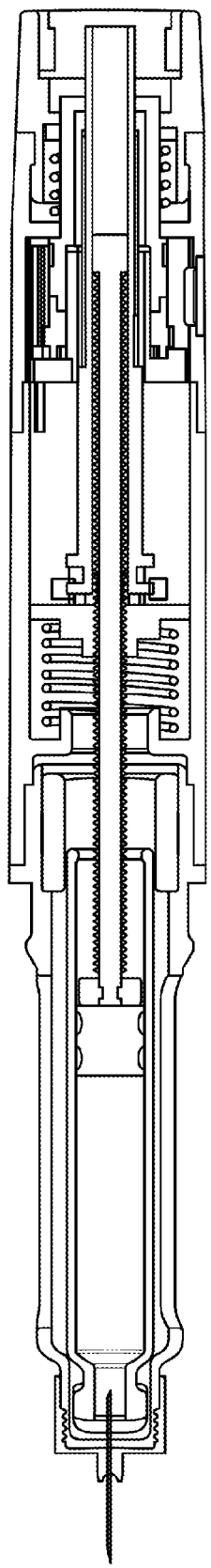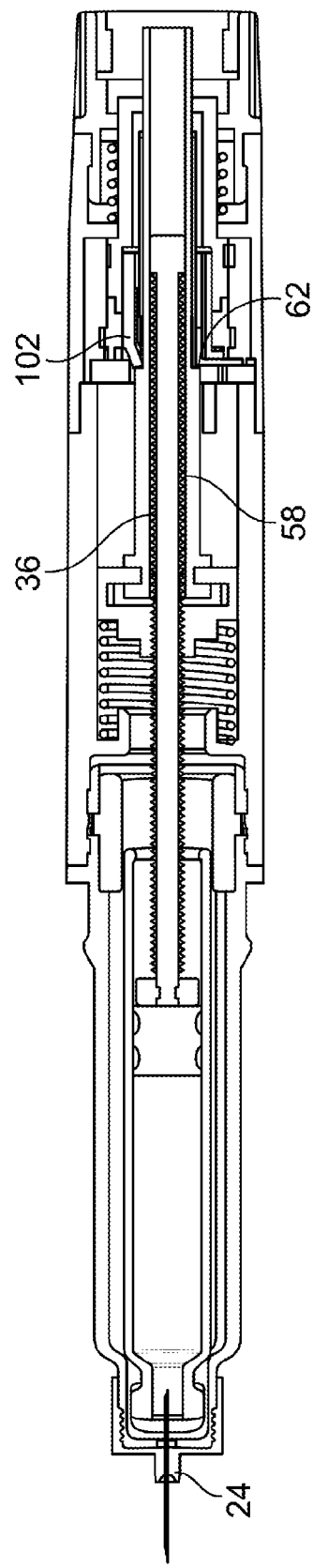
FIG. 8A
FIG. 8B

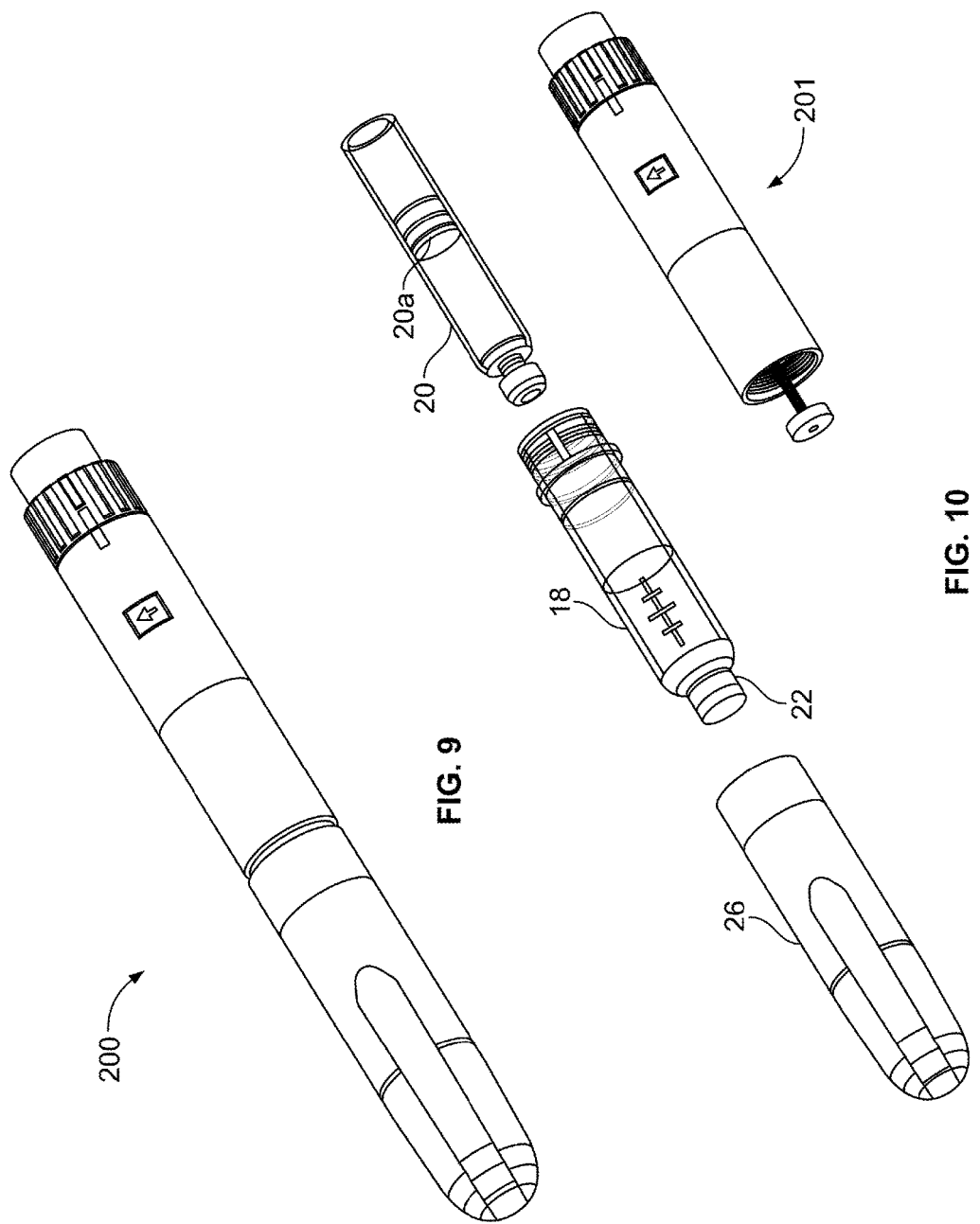

MEDICAMENT DELIVERY DEVICE

CROSS REFERENCE TO RELATED APPLICATIONS

The present application is a continuation-in-part of of U.S. patent application Ser. No. 14/449,671, filed Aug. 1, 2014, which is a continuation of U.S. patent application Ser. No. 13/896,639, filed May 17, 2013, now U.S. Pat. No. 8,827,962, which is a continuation of U.S. patent application Ser. No. 13/203,040, filed Jan. 31, 2012, now U.S. Pat. No. 8,491,536, which is a U.S. National Phase Application pursuant to 35 U.S.C. §371 of International Application No. PCT/US2010/060022 filed Dec. 13, 2010, which claims priority to Swedish Patent Application No. 0950958-9 filed on Dec. 15, 2009. The entire disclosure contents of these applications are herewith incorporated by reference into the present application.

TECHNICAL AREA

The present invention relates to a medicament delivery device comprising a dose setting function.

BACKGROUND

Medicament delivery devices such as injectors are sometimes provided with functions where a specific dose can be set by the user, which dose may be varied within a range.

Quite often this dose setting function is performed by turning a knob or wheel at the distal end of the device whereby it is moved in the distal direction. When performing a subsequent injection, the knob is pushed linearly in the proximal direction. One such injector is disclosed in the document U.S. Pat. No. 6,221,053 in which the distal dose knob of the injector is threaded out of a rod barrel tube as a dose is set. Thus the distance the knob is moved in the distal direction is directly related to the dose quantity to be delivered.

One drawback with that type of solution is that if larger doses are to be delivered the dose knob has to be moved quite a long distance in the distal direction, which means that it might be difficult for a user to push the dose knob in the proximal direction during injection.

SUMMARY

The aim of the present invention is to remedy the drawbacks of the state of the art medicament delivery devices and to provide a device by which it is possible to set a desired or required dose in a simple and intuitive way.

This aim is obtained by a medicament delivery device according to the features of the independent patent claim. Preferable embodiments of the invention are subject of the dependent patent claims.

Another aim of the present invention is to provide a dose injection button locking feature that reliably releases the dose button to an activated state when a user is ready to set a second and/or subsequent doses for injection. Failure to unlock the dose button, and concurrently the lead screw, reliably each time a dose is to be set will present a potentially dangerous situation in that a user may not be able to set and administer needed subsequent doses of medicament from the drug delivery device. The drug delivery device must be reliably unlocked after each administered dose by dialing the dose setting knob to an initial start position or to a zero dose setting causing the dose button to pop out rearwardly in the distal direction away from the outer housing of the delivery device.

According to a main aspect of the invention it is characterised by a medicament delivery device comprising a housing having opposite distal and proximal ends; a medicament container holder releasably connected to said housing; a medicament container arranged inside said medicament container holder; a threaded plunger rod arranged to pass through a first inner wall of the housing and arranged to act on a stopper in the medicament container; a lead screw member coaxially connected to the threaded plunger rod by co-acting first slidably-and-rotatably-locked means; wherein said device further comprises a nut coaxially connected to the threaded plunger rod by a treaded engagement between them, connected to the lead screw member by co-acting non-slidable-and-rotatable means, and connected to the housing by co-acting second slidably-and-rotatably-locked means; a primary dose member coaxially rotatable on the lead screw member when the device is in a non-activated state and connected to the lead screw member by co-acting third slidably-and-rotatably-locked means when the device is in an activated state; a locking member fixedly connected to the housing and releasably connected to the lead screw member by co-acting locking means; a first spring force means arranged between the first inner wall of the housing and the nut, wherein the first spring force means is in a pre-tensioned state when said locking means are engaged and the device is in the non-activated state; a secondary dose member rotatably connected to said primary dose member via a pinion gear; dose setting means connected to the primary dose member by co-acting fourth slidably-and-rotatably-locked means, such that when the device is to be set from the non-activated state to the activated state, the dose setting means are manually manipulated in a pre-determined direction, whereby the locking means are released and the lead screw member is distally moved a pre-determined distance by the first spring force means independent of the size of a dose to be set.

According to a further aspect of the invention, said primary and said secondary dose members are provided with indicia.

According to another aspect of the invention, the locking means comprises a proximally pointing and radial flexible lever arranged on the locking member, an annular ledge on the circumferential surface of the lead crew member, and the circumferential inner surface of the secondary dose member; such that when the first spring force means is in a pre-tensioned state, the circumferential inner surface of the secondary dose member forces the flexible lever radial inwardly in contact with the ledge; and when the dose setting means are manually manipulated, the secondary dose member is rotated to a position wherein the flexible lever is radial outwardly flexed into a longitudinal groove on the inner circumferential surface of the secondary dose member.

According to yet a further aspect of the invention, the locking member comprises on its distal circumferential surface a distally pointing stop member, and wherein the secondary dose member comprises on its proximal circumferential surface a first and a second proximally pointing stop members arranged to interact with the stop member of the locking member.

According to yet another aspect of the invention, the non-slidable-and-rotatable means comprises ratchet arms and radial inwardly directed arms on the nut, grooves on the outer circumference of wheels on the proximal end of the lead screw member, and an annular groove between the wheels, wherein the ratchet arms cooperate with the grooves for giving an audible signal when the lead screw member is rotated; and wherein the radial inwardly directed arms cooperate with the annular groove such that the lead screw member and the nut are slidably locked and rotatable in relation to each other.

According to a further aspect of the invention, the first slidably-and-rotatably-locked means comprises radial inwardly directed ledges on the inner surface of the proximal end of the lead screw member, and longitudinally extending grooves on the plunger rod, wherein the grooves cooperate with the radial inwardly directed ledges such that the lead screw member and the plunger rod are rotationally locked and slidable in relation to each other.

According to another aspect of the invention, the second slidably-and-rotatably-locked means comprises grooves on the outer circumferential side surface of the nut, and longitudinal ribs on the inner surface of the housing, wherein the grooves cooperate with the longitudinal ribs such that the nut and the housing are rotationally locked and slidable in relation to each other.

According to yet a further aspect of the invention, the third slidably-and-rotatably-locked means comprises splines on the outer circumferential surface of the lead screw member, and corresponding splines arranged on the inner circumferential surface of the primary dose member, wherein the splines cooperate with corresponding splines such that the lead screw member and the primary dose member are rotationally locked and slidable in relation to each other.

According to yet another aspect of the invention, the dose setting means comprises a clutch plate provided with a first annular ratchet, a dose setting knob provided with a second annular ratchet, and a second spring force means arranged between a second inner wall of the housing and a proximal surface of the clutch plate, such that clutch plate is distally urged and the first and the second ratchet are abutting each other, and which dose setting knob protrudes through the distal end of the housing.

According to a further aspect of the invention, the fourth slidably-and-rotatably-locked means comprises longitudinally extending grooves on the outer circumferential surface of the primary dose member, and radial inwardly directed protrusions on the inner surface of the clutch plate, wherein the longitudinally extending grooves cooperate with radial inwardly directed protrusions such that the primary dose member and the clutch plate are rotationally locked and slidable in relation to each other.

According to another aspect of the invention, the plunger rod is arranged to be proximally moved a distance corresponding to a set dose to be delivered by manually manipulating the dose setting knob when the device is in the activated state.

Yet another aspect of the the invention relates to reliably unlocking the dose injection button and lead screw when the dose setting mechanism transitions from a non-activated to an activated state. The dose setting mechanism includes a housing having a longitudinal axis, a lead screw positioned with the housing, and a locking member rotationally and slidably fixed to the housing, the locking member comprising a locking slot. A a dose member assembly is included in the housing having a biasing element, an inner sleeve and an outer sleeve, where the dose member assembly is arranged coaxially around the locking member and the lead screw, the biasing element is operatively engaged with the locking member and the inner sleeve, and where the inner sleeve has a radially projecting key configured to travel in the locking slot to engage the lead screw to prevent axial movement of the lead screw when the dose setting mechanism is in the non-activated state. Preferably, the locking slot maybe L-shape.

The biasing element may be a spring, preferably a torsional spring, that exerts a rotational force on the inner sleeve. The key on the inner sleeve can be configured to disengage from the leadscrew when the dose setting member transitions from the non-activated state to an activated state thereby releasing or unlocking the dose injection button.

In one particular advantageous embodiment of the dose setting mechanism, the key comprises a chamfer projecting distally and configured to engage a proximal edge of an axial rib positioned on an outer surface the lead screw such that axial movement of the lead screw in a proximal direction causes rotation of the inner sleeve. Additionally the the inner sleeve may include a radially projecting protrusion on its outer surface that engages a radially projecting rib located on an inner surface of the outer sleeve such that rotation of the outer sleeve causes rotation of the inner sleeve.

There are a number of advantages with the present invention. Because the lead screw, e.g. the manually operating delivery means, protrudes outside the housing with the same length independent of the set dose quantity the manual dose delivery operation is the same independent of set dose, i.e. the lead screw member has always the same position when a dose has been set.

Compared to the state of the art medicament delivery devices, this solution is a great advantage for the user or patient who suffers of dexterity problems. Also when not in use, the lead screw member is inside the medicament delivery device and locked. The unlocking of the lead screw member is performed when said dose setting knob is turned to an initial position, preferably a zero-dose position.

These and other features and advantages will become apparent from the detailed description and from the accompanying drawings.

BRIEF DESCRIPTION OF THE FIGURES

In the detailed description reference will be made to the accompanying drawings in which FIGS. 1a, b are a cross-sectional view of a medicament delivery device according to the present invention;

FIGS. 6, 7a, 7b, 8a, and 8b are cross-sectional view of different functional positions.

FIG. 9 is a perspective view of a possible embodiment of the present invention;

FIG. 10 is a partially exploded view of the embodiment shown in FIG. 9;

DETAILED DESCRIPTION

Figure 1:
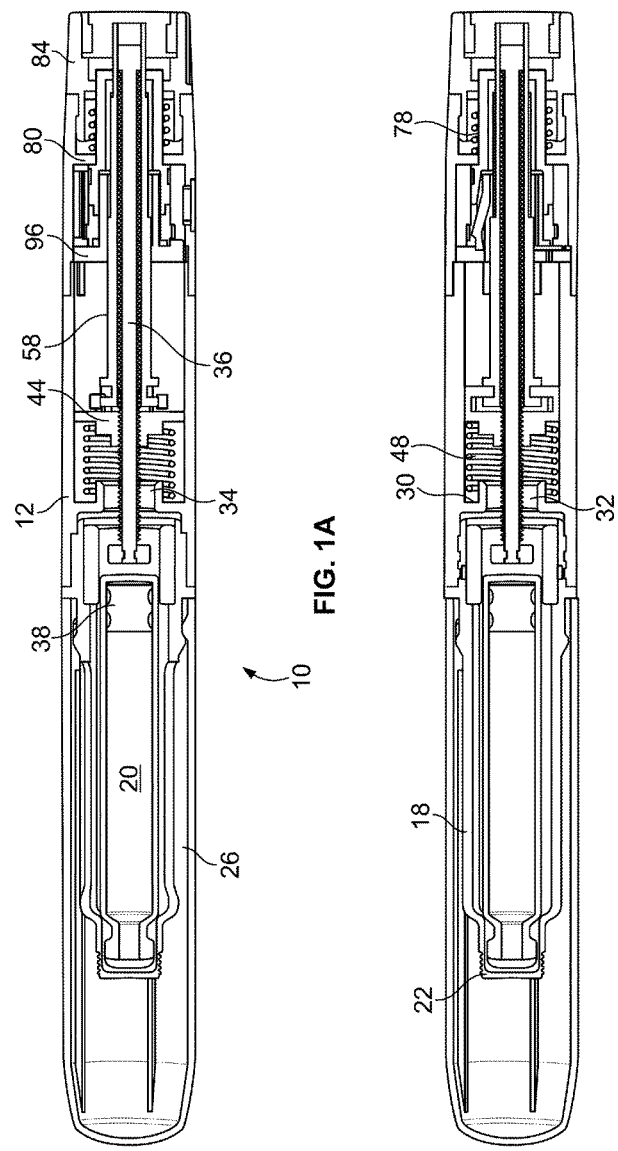

In the present application, when the term "distal part/end" is used, this refers to the part/end of the injection device, or the parts/ends of the members thereof, which under use of the injection device is located the furthest away from the medicament injection site of the patient. Correspondingly, when the term "proximal part/end" is used, this refers to the part/end of the injection device, or the parts/ends of the members thereof, which under use of the injection device is located closest to the medicament injection site of the patient.

The medicament delivery device 10 according to the drawings comprises a generally elongated housing 12 having opposite distal and proximal ends. The elongated housing 12 being e.g. divided in a proximal 12a and a distal part 12b. The proximal end of the housing 12 is arranged with fastening means such as e.g. threads 14 on its inner surface, which fastening means cooperate with corresponding fastening means such as outwardly threads 16 on a distal end of a medicament container holder 18, providing a releasable connection. Inside the medicament container holder 18 a medicament container 20 can be placed. The proximal end of the medicament container holder 18 is arranged with a threaded neck 22 for connection of a medicament delivery member such as an injection needle 24, a mouthpiece, a nozzle or the like, FIG. 2.

When received by a user, the medicament delivery device 10 is provided with a releasably attachable protective cap 26. At the distal end of the medicament container holder 18 a sleeve-shaped container support 28 is inserted for holding and supporting the medicament container 20 when inserted, FIG. 2. At the proximal end of the housing 12 a first inner wall 30 is arranged, which wall is provided with a central passage 32, FIG. 1B. The central passage 32 is arranged with a distally directed tubular flange 34, FIG. 1A. A threaded plunger rod 36 extends in the longitudinal direction through the central passage 32 with a proximal end adjacent a stopper 38 inside said medicament container 20, FIG. 1a. The proximal end of the plunger rod 36 is further arranged with a plunger rod tip 40, FIG. 2.

The device further comprises a lead screw member 58 coaxially connected to the threaded plunger rod 36 by co-acting first slidably-and-rotatably-locked means; and a nut 44 coaxially connected to the threaded plunger rod 36 by a treaded engagement between them. The nut 44 also being connected to the lead screw member 58 by co-acting non-slidable-and-rotatable means, and to the housing by co-acting second slidably-and-rotatably-locked means.

Figure 2:
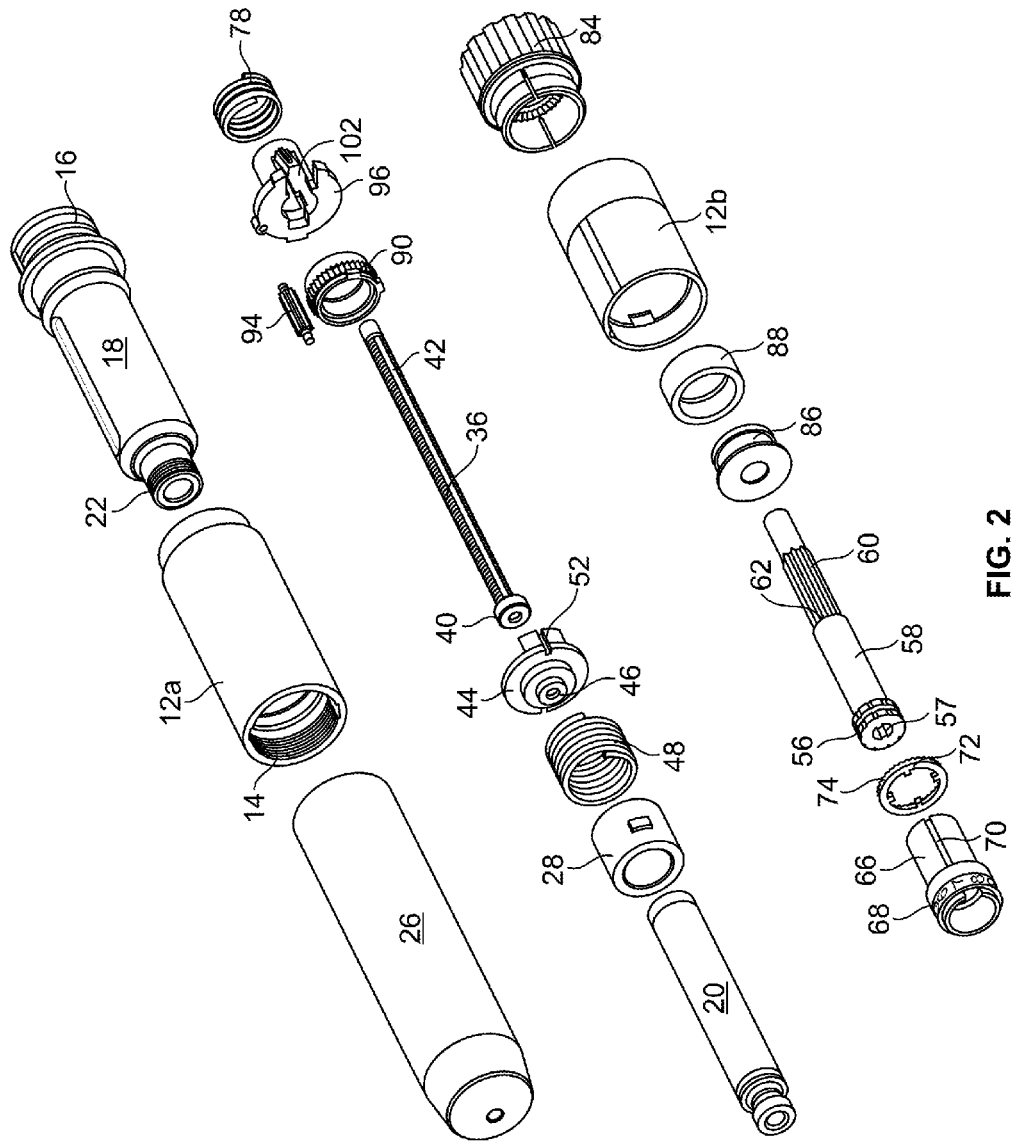
FIG. 2 is an exploded view of the medicament delivery device of FIGS. 1a, b.

The first slidably-and-rotatably-locked means comprises radial inwardly directed ledges 57 on the inner surface of the proximal end of the lead screw member 58, and longitudinally extending grooves 42 on the plunger rod 36, FIG. 2, wherein the grooves 42 cooperate with the radial inwardly directed ledges 57 such that the lead screw member 58 and the plunger rod 36 are rotationally locked and slidable in relation to each other.

Figure 3:
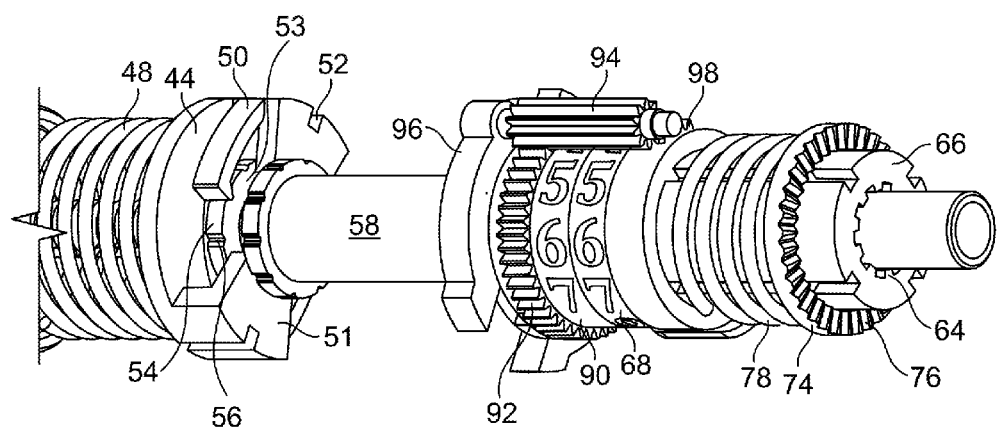
FIG. 3 is a detailed view of a dose-setting mechanism comprised in the present invention.

The non-slidable-and-rotatable means comprises ratchet arms 50 and radial inwardly directed arms 51 on the nut 44, grooves 56 on the outer circumference of wheels 54 on the proximal end of the lead screw member 58, and an annular groove 53 between the wheels 54, wherein the ratchet arms 50 cooperate with the grooves 56 for giving an audible signal when the lead screw member 58 is rotated; and wherein the radial inwardly directed arms 51 cooperate with the annular groove 53 such that the lead screw member 58 and the nut 44 are slidably locked and rotatable in relation to each other, FIG. 3.

The second slidably-and-rotatably-locked means comprises grooves 52 on the outer circumferential side surface of the nut 44, FIG. 3, and longitudinal ribs on the inner surface of the housing (not shown), wherein the grooves 52 cooperate with the longitudinal ribs such that the nut and the housing are rotationally locked and slidable in relation to each other.

The nut 44 comprises a threaded central passage 46 which cooperates with the threads of the plunger rod 36, FIG. 2, thereby forming the threaded engagement between them.

The device also comprises a primary dose member 66 coaxially rotatable on the lead screw member 58 when the device is in a non-activated state and connected to the lead screw member 58 by co-acting third slidably-and-rotatably-locked means when the device is in an activated state. The third slidably-and-rotatably-locked means comprises splines 60 on the outer circumferential surface of the lead screw member 58; and corresponding splines 64 arranged on the inner circumferential surface of the primary dose member 66, wherein the splines 60 cooperate with corresponding splines 64 such that the lead screw member 58 and the primary dose member 66 are rotationally locked and slidable in relation to each other, FIGS. 2 and 3.

The device further comprises: a locking member 96 fixedly connected to the housing 12 and releasably connected to the lead screw member 58 by co-acting locking means; a first spring force means 48 arranged between the first inner wall 30 of the housing 12 and the nut 44, wherein the first spring force means is in a pre-tensioned state when said locking means are engaged and the device is in the non-activated state; and a secondary dose member 90 rotatably connected to said primary dose member 66 via a pinion gear 94, FIG. 3.

The device also comprises dose setting means connected to the primary dose member 66 by co-acting fourth slidably-and-rotatably-locked means, such that when the device is to be set from the non-activated state to the activated state, the dose setting means are manually manipulated in a pre-determined direction, whereby the locking means are released and the lead screw member 58 is distally moved a pre-determined distance by the first spring force means 48 independent of the size of a dose to be set.

Figure 4:
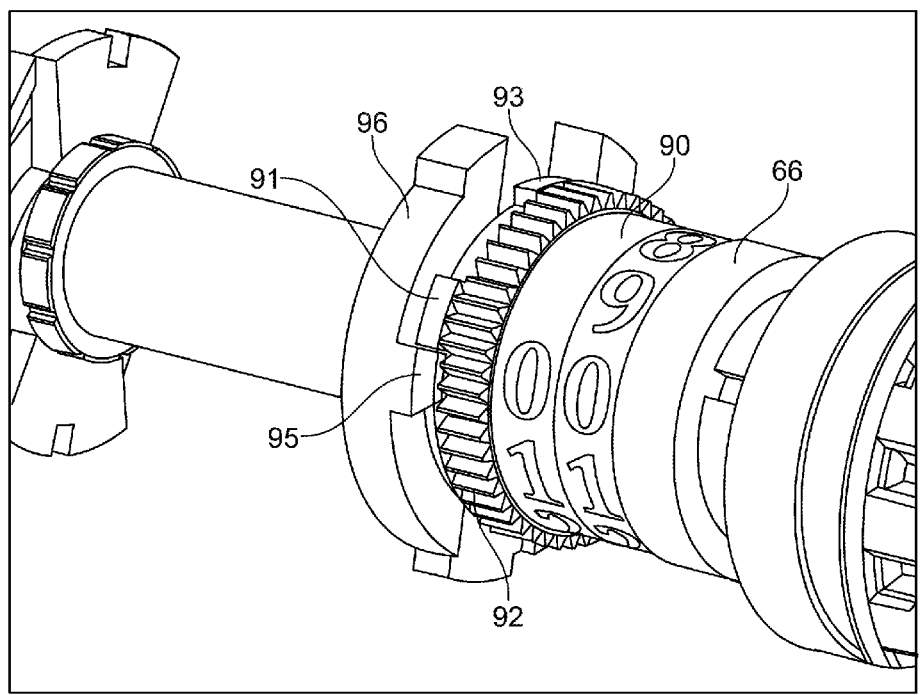
FIG. 4 is a further detailed view of the dose-setting mechanism comprised in the present invention.
Figure 5:
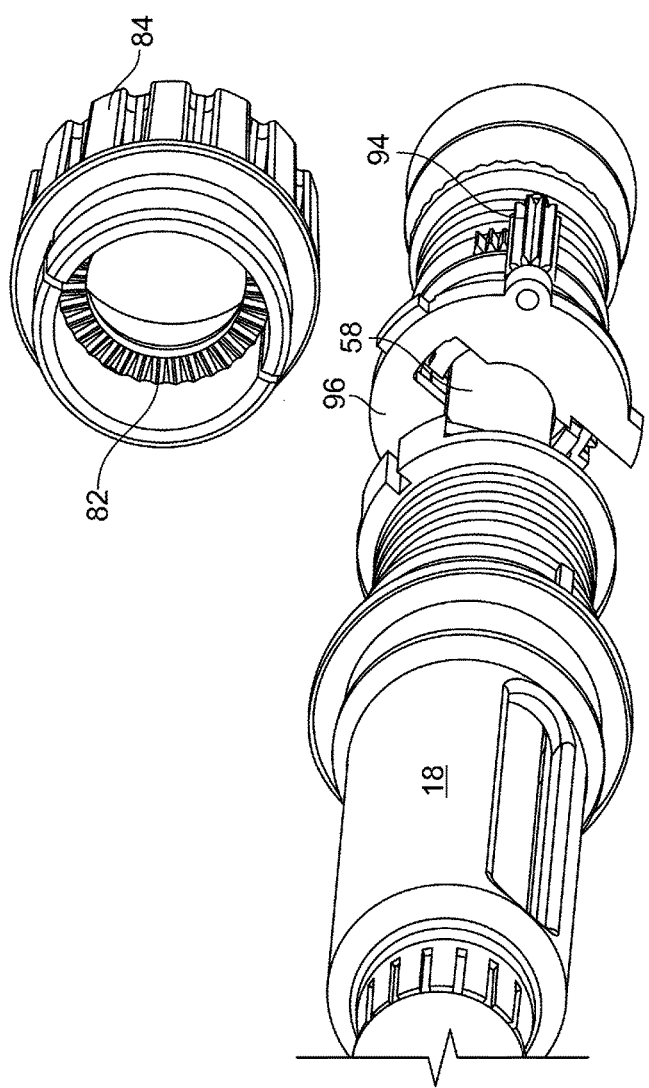
FIG. 5 is yet a further detailed view of the dose-setting mechanism comprised in the present invention.
Figure 6:
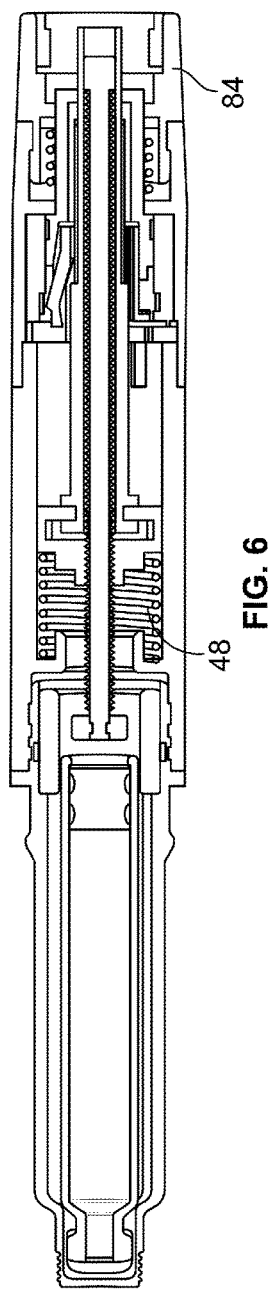

The dose setting means comprises a clutch plate 74 provided with a first annular ratchet 76, a dose setting knob 84 provided with a second annular ratchet 82, and a second spring force means 78 arranged between a second annular inner wall 80 of the housing and a proximal surface of the clutch plate 74, such that clutch plate 74 is distally urged and the first and the second ratchet 76, 82 are abutting each other, and which dose setting knob 84 protrudes through the distal end of the housing 12, FIGS. 1*a* and 4. The fourth slidably-and-rotatably-locked means comprises longitudinally extending grooves 70 on the outer circumferential surface of the primary dose member 66, and radial inwardly directed protrusions 72 on the inner surface of the clutch plate 74, wherein the longitudinally extending grooves 70 cooperate with radial inwardly directed protrusions 72 such that the primary dose member 66 and the clutch plate 74 are rotationally locked and slidable in relation to each other, FIGS. 2 and 3. The distal end of the lead screw member 58 protrudes through the dose setting knob 84, and is at its distal end arranged with a dose injection button 86, FIGS. 2 and 7*b*. Outside the dose injection button 86 a spin ring 88 is rotatably arranged, FIG. 2.

The locking means comprises: a proximally pointing and radial flexible lever 102 arranged on the locking member 96, an annular ledge 62 on the circumferential surface of the lead crew member 58, and the circumferential inner surface of the secondary dose member, FIG. 2. The secondary dose member 90 is also arranged with teeth 92 arranged around its circumference, which teeth cooperate with teeth 92 on the pinion gear 94, which is journalled in the housing as well as the locking member 96 via a locking lever bracket, FIG. 3. Further the primary dose member 66 is arranged with a gear segment 98, which also cooperate with the pinion gear 94, FIG. 3. A certain part of the lead screw member 58 is arranged with the splines 60 on its outer circumferential surface, FIG. 2; which splines 60 have a lesser diameter than the proximal part of the lead screw member 58, thereby creating the annular ledge 62, FIG. 2. The locking member 96 also comprises on its distal circumferential surface a distally pointing stop member 95, and the secondary dose member 90 comprises on its proximal circumferential surface a first 91 and a second 93 proximally pointing stop member 95 arranged to interact with the stop member 96 of the locking member, FIG. 4.

The proximal part of the primary dose member 66 and the secondary dose member 90 are arranged with a circumferential band containing numbers or indicia 68 which are used to indicate dose size through a dose window on the housing, as will be explained below, FIG. 3.

The device is intended to function as follows. When delivered to the user, the device is in the non-activated state wherein a medicament container 20 has been inserted in the medicament container holder 18 in the proximal end of the device, FIG. 1, the first spring force means 48 is in a pre-tensioned state and said locking means are engaged, wherein the circumferential inner surface of the secondary dose member 90 forces the flexible lever 102 radial inwardly in contact with the ledge 62.

When the device is to be used the protective cap 26 is removed and the dose setting means are manually manipulated for setting the device from the non-activated state to the activated state by rotating the dose setting knob 84 counter clockwise until activating indicia as e.g. two zeros are visible through the window of the housing 12. The rotation of the dose setting knob 84 causes the clutch plate 74 and thereby the primary dose member 66 to rotate due to the engagement between the co-acting fourth slidably-and-rotatably-locked means, and due to the connection between the first 76 and the second 82 ratchets. However, the lead screw member 58 is not rotated since the third slidably-and-rotatably-locked means 60, 64 are not in engagement, i.e. the splines 60 on the outer circumferential surface of the lead screw member 58 and the corresponding splines 64 arranged on the inner circumferential surface of the primary dose member 66 are not in engagement. The secondary dose member 90 also rotates due to the connection between the gear segment 98 of the primary dose member 66 and the teeth 92 of the secondary dose member 90 through the pinion gear 94. The rotation of the secondary dose member 90 is stopped when its second proximally pointing stop member 93 abuts the distally pointing stop member 95. This causes a longitudinal groove on the inner circumferential surface (not shown) of the secondary dose member 90 to be aligned with the flexible lever 102 whereby the flexible lever 102 is radial outwardly flexed into the groove and thereby moved out of contact with the ledge 62 of the lead screw member 58. This causes the lead screw member 58 to move a pre-determined distance in the distal direction due to the force of the spring 48 acting on the nut 44, which in turn is attached to the lead screw member 58. The splines 60 on the outer circumferential surface of the lead screw member 58 and the corresponding splines 64 arranged on the inner circumferential surface of the primary dose member 68 are then engaged to each other. Because of the movement of the nut 44, the plunger rod 36 is also moved. The distal end of the lead screw member 58 and its dose injection button 86 now protrude distally out of the housing said predetermined distance and independent of the size of the dose to be set.

Figure 7A:
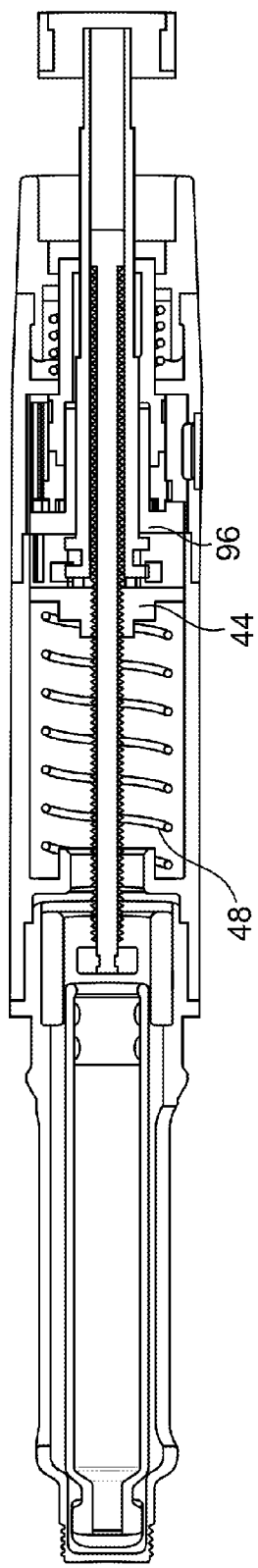
Figure 7B:
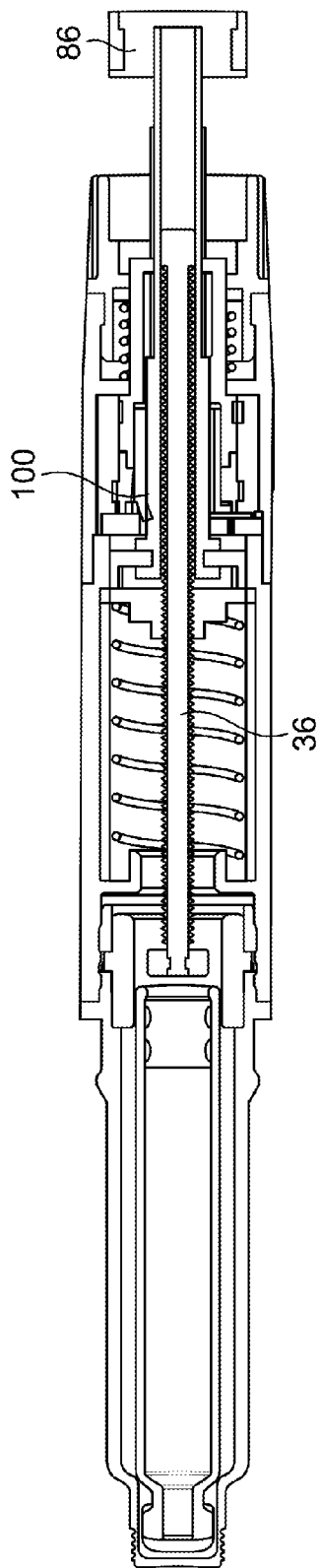

The device is now in the activated state and ready for setting a required dose of medicament, FIGS. 7*a* and 7*b*.

When setting a dose, the plunger rod 36 is arranged to be proximally moved a distance corresponding to a set dose to be delivered by manually manipulating the dose setting knob 84. The dose setting knob 84 is rotated in the clockwise direction which also rotates the primary dose member 66 clockwise indicating the dose that is being dialed. At the same time the primary dose member 66 rotates the lead screw member 58 clockwise due to the engagement between the co-acting third slidably-and-rotatably-locked means 60, 64; and the lead screw member 58 rotates the plunger rod 36 due to the engagement between the co-acting first slidably-and-rotatably-locked means, driving the plunger rod 36 through the nut 44 because of the threaded engagement between them, thereby moving the plunger rod 36 proximally. The secondary dose member 90 also rotates due to the connection between the gear segment 98 of the primary dose member 66 and the teeth 92 of the secondary dose member 90 through the pinion gear 94. The rotation of the secondary dose member 90 is stopped when its first proximally pointing stop member 91 abuts the distally pointing stop member 95, which indicates the maximum dose the device can deliver e.g. two indicia as e.g. a seven and a zero are visible through the dose window. In any case, the set dose is visible through the dose window of the housing. At this point the device is ready for an injection.

Moreover, if the user attempts to dial past the maximum dose the device can deliver or if the user attempts to dial pass the activating indicia, the connection between the first annular ratchet 76 and the second annular ratchet will function as a clutch.

When the dose is set, a medicament delivery member 24 is attached to the proximal end of the device, such as e.g. an injection needle. It is however to be understood that other types of medicament delivery members may be used in order to deliver a dose of medicament. The medicament delivery member 24 is then placed at the delivery site and the user presses the dose injection button 86 in the proximal direction the predetermined distance that the distal end of the lead screw member 58 and its dose injection button 86 protrudes distally out of the housing and which said predetermined distance is independent of the size of the dose to be delivered. This causes the lead screw member 58 to move in the proximal direction as well as the nut 44 and the plunger rod 36. This proximal movement of the plunger rod 36 causes it to act on the stopper 38 of the medicament container 20 whereby a dose of medicament is expelled through the medicament delivery member 24. When the lead screw member 58 has reached a certain distance inside the housing, the flexible lever 102 of the locking member 96 is again moved in contact with the ledge 62 of the lead screw member 58, FIG. 8. The medicament delivery member may now be removed and discarded.

When a subsequent dose is to be performed, the above described procedure is performed and can be repeated until the medicament container is emptied.

Another embodiment of the invention is presented in FIGS. 9-19. This embodiment 200 differs slightly in structure and operation from that of the above-described embodiments in that this version of the device allows a user to set only one preset, pre-selected or pre-determined dose setting. For example, the device 200 could be manufactured such that a single fixed dose of 5 units or 10 units is preselected and the user would not be able to dial a dose greater than or less than the one single dose. In other words, the device does not have variable dose setting functionality, instead this type of device is referred to as a fixed dose device.

Figure 11:
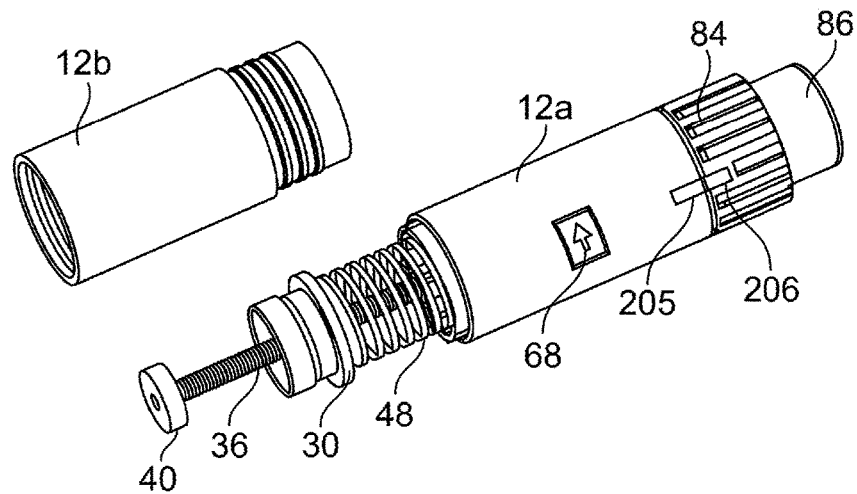
FIG. 11 is a partially exploded perspective view of the dose setting mechanism of the embodiment shown in FIG. 9.
Figure 12:
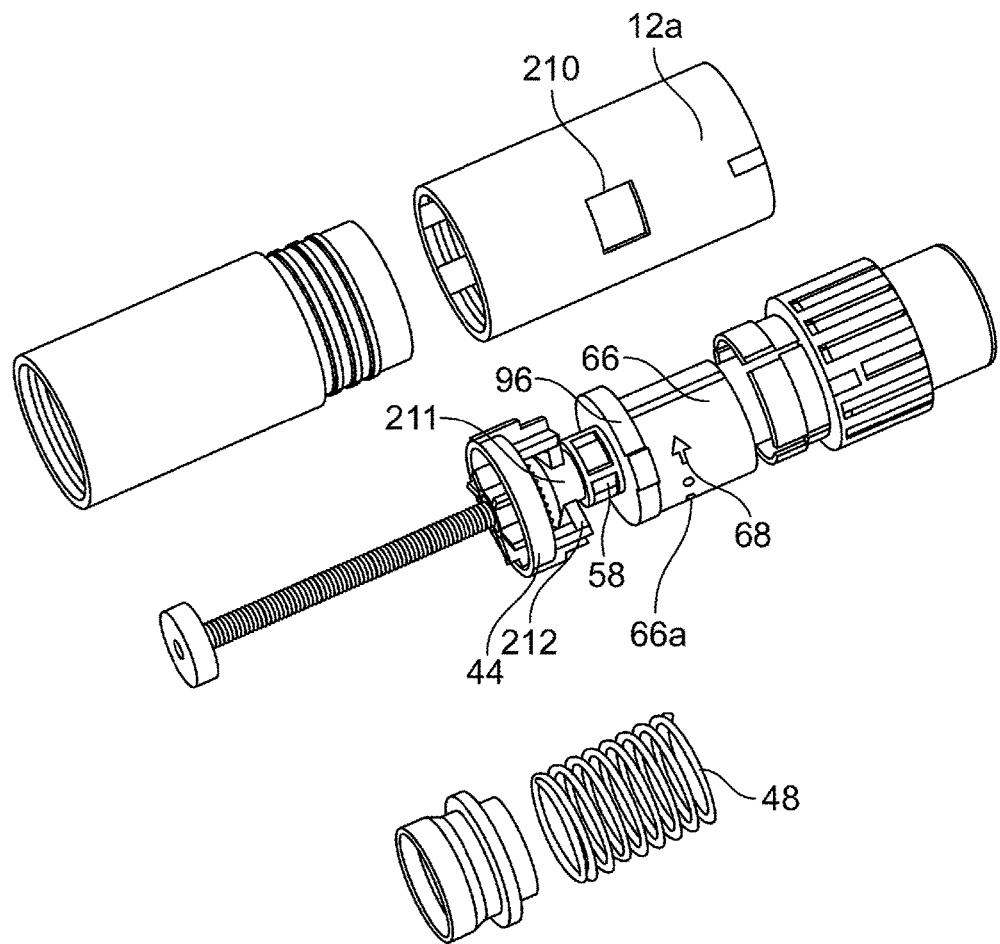
FIG. 12 is a further exploded perspective view of the dose setting mechanism of the embodiment shown in FIG. 9.

In one possible embodiment of the fixed dose design, device 200 has a dose setting mechanism 201 shown in FIG. 10 and in more detail in FIGS. 11-12. The distal part 12*a* of the elongated housing 12 contains a window 210 that allows a user to view and/or feel indicia 68 printed or otherwise located on the outer surface 66*a* of the dose member 66. As illustrated in the figures, an arrow can be used to provide the user with a visual clue or prompt as to what direction to rotate dose setting knob 84 when the dose setting mechanism is in the activated state. The activated state is achieved when the user rotates the dose setting knob to the zero dose position, which as exemplified in the figures can be seen as the arrow or as a "0" or any other desired indicia to indicate the starting position.

Figure 16:
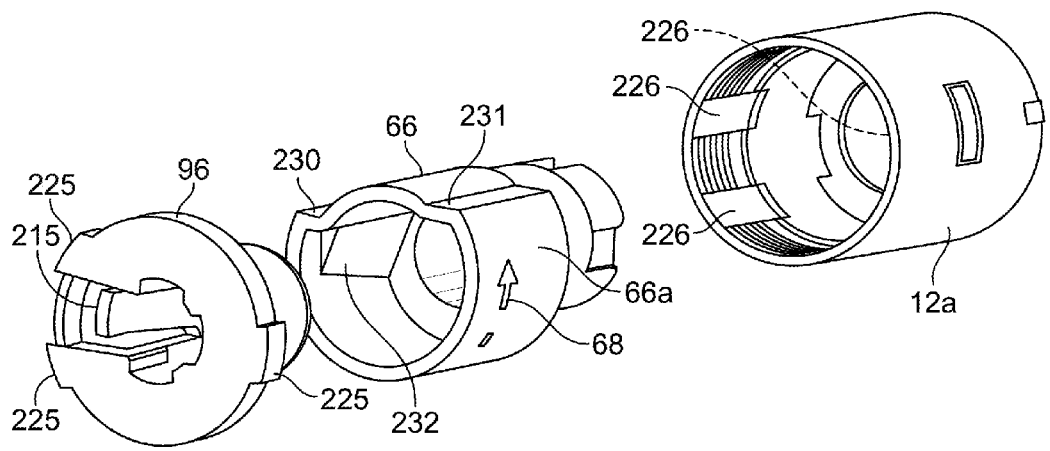
FIG. 16 is a close up perspective view of the locking member, dose member and distal housing portion of the embodiment shown in FIG. 9.
Figure 18:
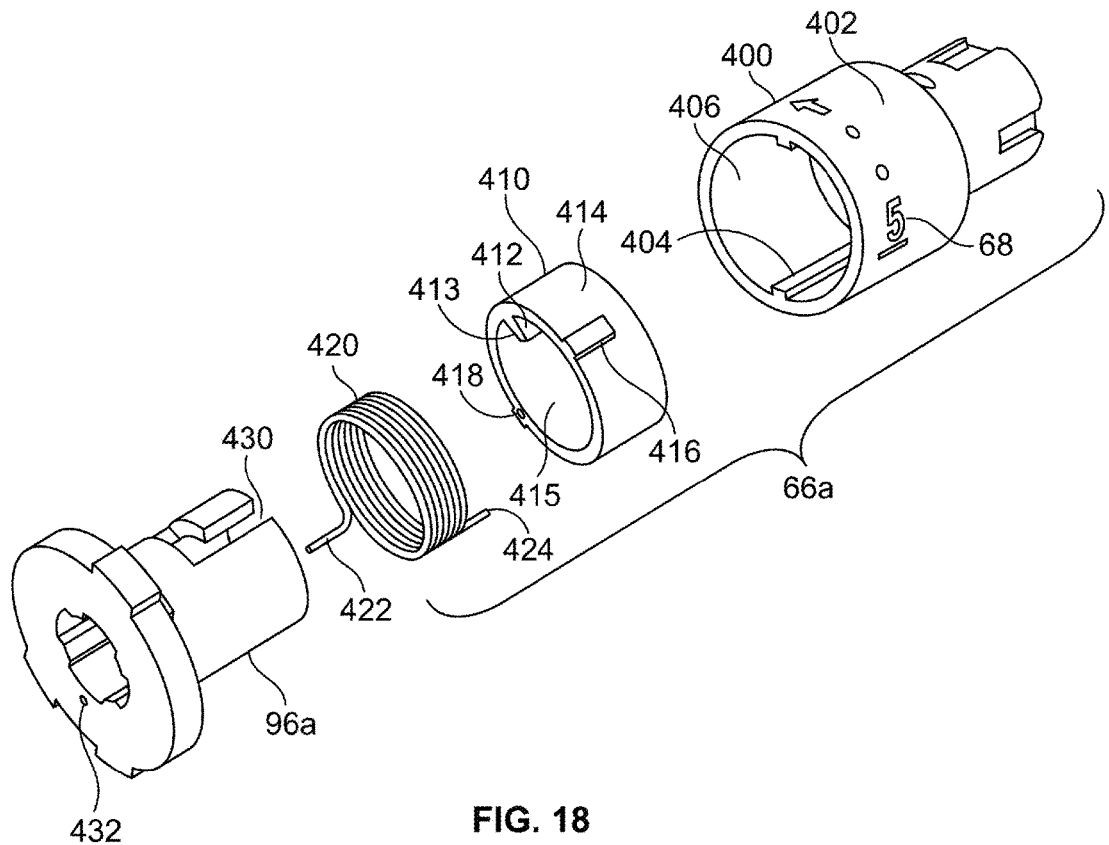
FIG. 18 is a close up perspective and exploded view of a portion of the dose setting mechanism having a modified locking member and a dose member assembly.
Figure 19:
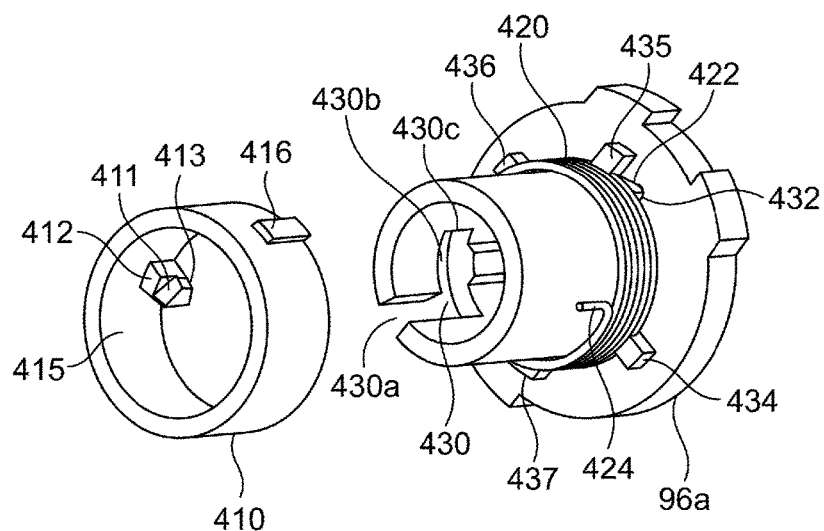
FIG. 19 is a close up perspective and exploded view of a portion of the modified locking member and a dose member assembly shown in FIG. 18.

In the non-activated state, the flexible lever 215 of locking member 96 is engaged with ledge 62 on lead screw 58. This is best shown in FIG. 18 where the upper figure illustrates the activated state where the dose button is moved distally outward (so-called "popped out") from the dose setting knob 84 and housing 12*a* as a result of the axial movement in the distal direction of lead screw 58 by the biasing force exerted by biasing member 48, shown as a compression spring. FIG. 11 illustrates indicia 205 and 206 being aligned when the device is in the activated state with the button 86 "popped out." The lower figure of FIG. 18 illustrates the dose setting mechanism 201 in the non-activated state where spring 48 is compressed (pre-tensioned) by the forward or proximal movement of lead screw 58 during dose delivery. The lead screw 58 is prevented from moving distally by the engagement of lever 215 with ledge 62, where the lever 215 is biased radially inward by the dose member 66 and in particular by the cam surface 232 on the inside surface of dose member 66. This is best shown in FIG. 16. This cam surface 232 acts as a bearing surface against the outside surface of lever 215 to deflect the lever 215 inwardly so that it remains engaged with ledge 62.

Figure 13:
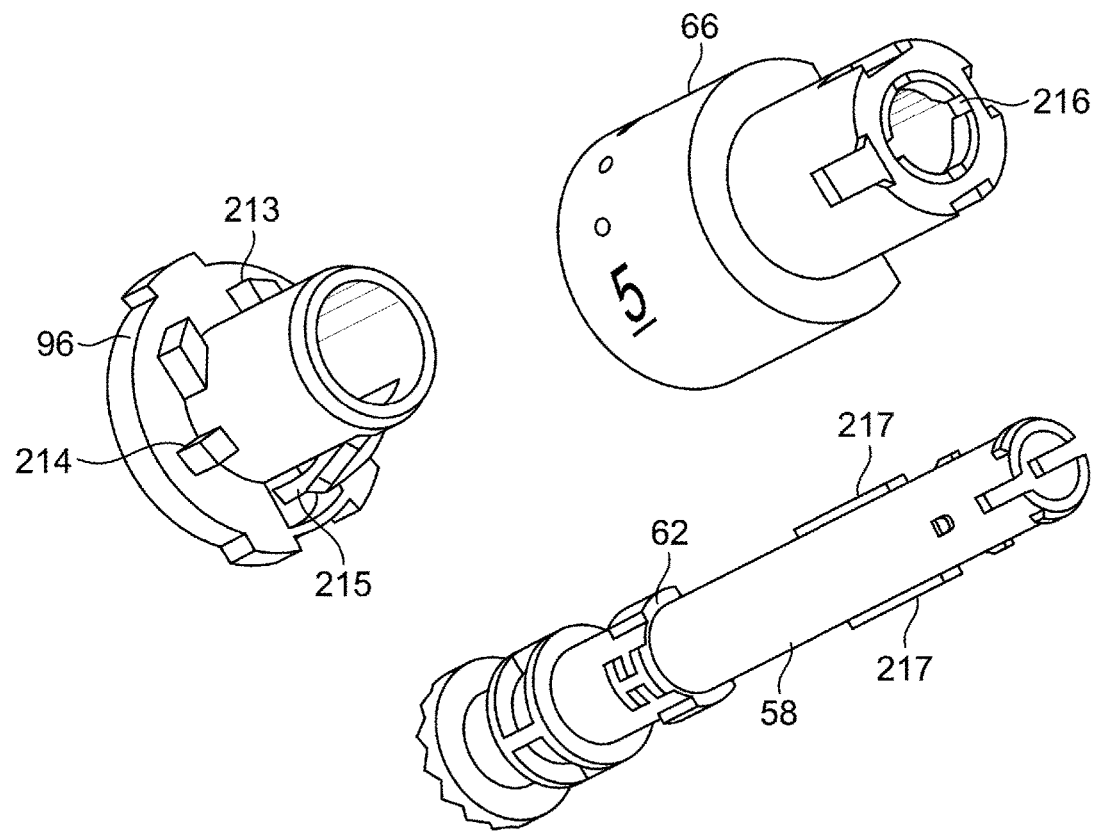
FIG. 13 is a close up perspective view of the locking member, lead screw and dose member of the embodiment shown in FIG. 9.
Figure 15:
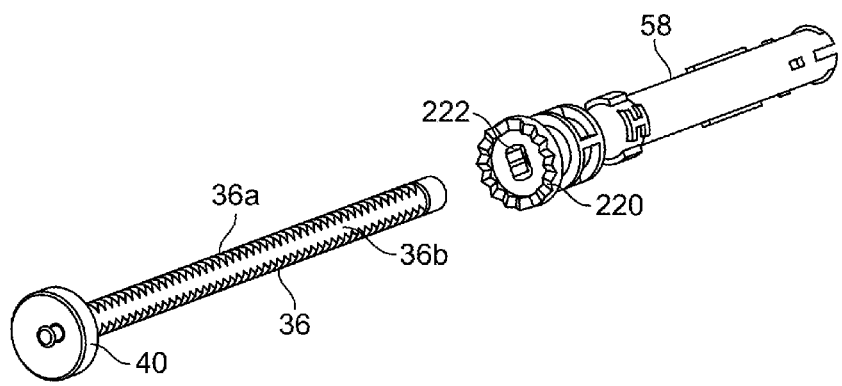
FIG. 15 is a close up perspective view of the locking member and plunger rod of the embodiment shown in FIG. 9.

FIG. 16 shows the relationship of locking member 96, dose member 66 and distal housing 12*a*. As mentioned, locking member 96 is rotationally and axially fixed relative to the housing 12*a*. This fixation is a result of the engagement of radially projecting ribs 225 on locking member 96 that engages corresponding slots 226 on the inside surface of housing 12*a*. Dose member 66 has two rotational stops 230 and 231 that engage corresponding stops 213 and 214 on the distal side of locking member 96 (see FIG. 13). FIG. 13 illustrates axial ribs 217 that engage with slots 216 on dose member 66 when the device is in the activated state. This engagement rotationally fixes the dose member 66 to the lead screw 58 such that rotation of the dose setting knob 84 causes the dose member 66 to rotate as well as lead screw 58. FIG. 15 illustrates the relationship of the plunger rod 36 to the lead screw 58. In the particular embodiment shown the plunger rod 36 is shown with a non-circular cross-section having a pair of opposed flat surfaces 36*b* with threaded segments 36*a* between each flat portion 36*b*. The proximal through hole 222 of lead screw 58 is configured to match the non-circular cross-sectional shape of plunger rod 36 such that the plunger rod is rotationally fixed to the lead screw 58, but can move or slide axially relative to the lead screw.

Figure 14:
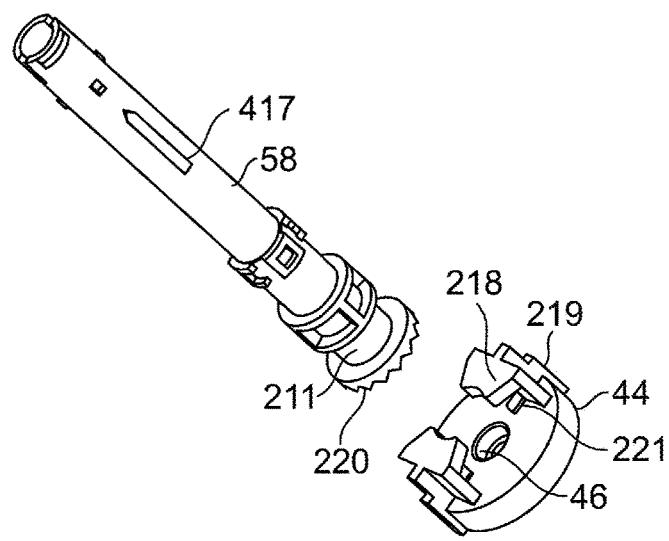
FIG. 14 is a close up perspective view of the nut and lead screw of the embodiment shown in FIG. 9.

The plunger rod 36 is threadedly engaged with nut 44 through threaded through hole 46 (see FIGS. 12 & 14). Nut 44 is rotational fixed to the housing by the engagement of radially extending ribs 219 that cooperate with corresponding slots on the inside of the housing. These slots are longitudinal in length and are configured to allow the nut 44 to slide axially relative to the housing. The nut 44 is fixed to the proximal end of lead screw 58 through the engagement of finger 218 in radial groove 211 at the proximal end of lead screw 58. This groove 211 is sized with sufficient axial width such that the lead screw 58 and the distal face of the nut 44 can move axially relative to each other during dose setting. During dose setting the lead screw 58 is rotated relative to nut 44, which is rotationally fixed to the housing. The spring 48 exerts a biasing force in the proximal direction against the proximal face of the nut 44 causing two opposed distally projecting ratchet teeth 221 to engage complimentary proximally projecting ratchet teeth 220 located at the proximal end of the lead screw 58. As the lead screw 58 is rotated the ratchet teeth 220 rotate relative to the stationary ratchet teeth 221 causing the teeth 220 to ride up and over teeth 221. This riding up and over motion moves the lead screw axially back and forth within groove 211. The nut is held in the groove by finger 218 (see FIG. 12).

Figure 17:
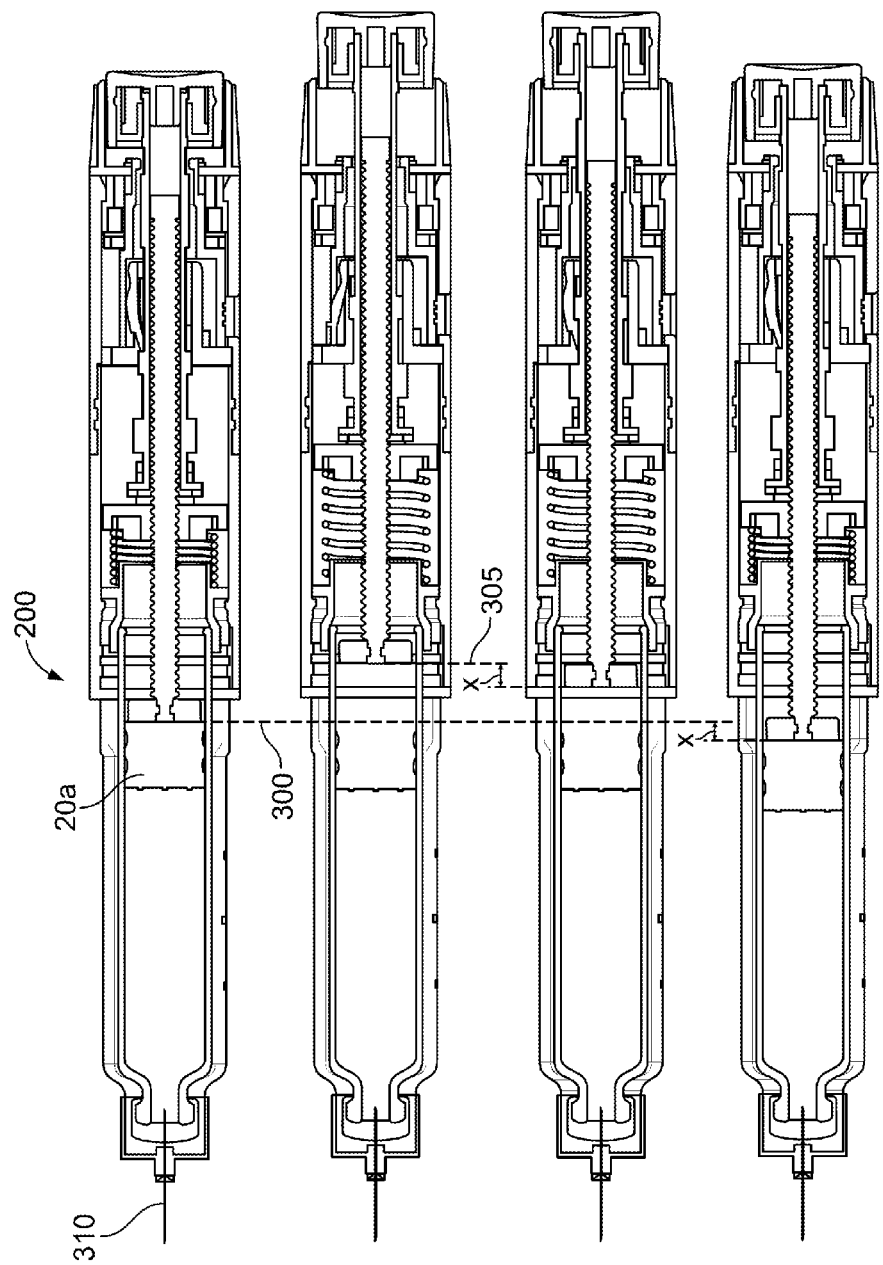
FIG. 17 are cross-sectional views of the sequence of operation of the embodiment shown in FIG. 9.

FIG. 17 illustrates the sequence of operation of device 200. The top figure shows the device in a non-activated state, for example, immediately after dose delivery. Here the dose button is pushed in (i.e., not "popped out") and the spring is in the pre-tensioned compressed state being held in this compressed state by the engagement of the flexible lever on the locking member locked with the ledge on the lead screw. The next figure shows the device in the activated state when the dose setting knob is rotated to the zero dose or starting position, e.g., where the arrow is shown in the housing window. The transition from the non-activated to the activated state causes the lead screw, plunger rod and nut to all move distally by the biasing force exerted by the spring. The spring moves these three components because the dose setting knob and dose member were rotated such that the dose member no longer biases the flexible lever inward and thus it disengages from the ledge on the lead screw. The distance these three components move is always the same distance distally as indicated by the distance between lines 300 and 305. This moves the plunger rod off of and away from cartridge piston 20*a* by the same distance. At this point, when the device is in the activated state, a dose can be set by rotating the dose setting knob. Since the plunger rod was moved distally off the cartridge piston when the zero dose position was obtained, the axial movement of plunger rod in the proximal direction does not move (or contact) the bung.

Setting a dose also rotates the dose member, which then biases the flexible lever inwardly. The third figure in FIG. 17 represents the device with a dose set. Setting the dose caused the plunger rod to screw through the nut moving proximally a distance X. To deliver the set dose the user pushes the dose button proximally which pushes the lead screw, nut and plunge rod proximally as well. These three components move proximally and as the lead screw is pushed forward proximally, the flexible levers on the locking member that is axially fixed relative to the housing, flex over the ledge on the outside of the lead screw and causes the lead screw to be locked in the original most forward or proximal position, i.e., the non-activated state. As the lever re-engages the ledge on the lead screw, the spring is returned to the pre-tensioned state. As illustrated in the bottom figure of FIG. 17, the plunger rod moves an additional distance X representing and proportional to the dose set. This in turn moves the cartridge piston the same distance X and thus expels that amount of medicament from the proximal end of the cartridge through the injection needle 310.

An alternative to locking member 96 and dose member 66 as described above is presented in FIGS. 18-19, where an alternative design of the locking member 96a is operatively engaged with dose member 66a to provide a lock mechanism that reliably unlocks the dose injection button and the lead screw 58 so subsequent doses can be set, as will be further described below. Dose member assembly 66a comprises at least three components, a biasing element 420, an inner sleeve 410 and an outer sleeve 400. The biasing element is shown as a torsional spring, however, other types or designs of springs may be used. Likewise, a non-spring component could be used, for example, flexible fingers, spring washers, and the like materials can be used to provide the required rotation forces necessary to bias the key 412 to stay within the transverse portion 430b of the locking slot 430.

The inner and outer sleeves, 410 and 400, preferably have a circular cross-section and are concentrically positioned with respect to each other such that the outer sleeve 400 is coaxially arranged and covers the inner sleeve 410. The outer sleeve 400 has an outer surface 402 that may contain indicia 68 as earlier described. The outer sleeve 400 also has an inner surface 406 that contains at least one radially projecting rib 404 positioned longitudinally along the inner surface 402. This rib 404 is configured to interact with protrusion 416 on the outer surface 414 of inner sleeve 410 when the dose setting knob 84 is rotated to set a dose of medicament, which also causes outer sleeve 400 to rotate.

Inner sleeve 410 has an inner surface 415 that contains a radially projecting key 412 having a proximally facing stop face 413. This stop face 413 is configured to abut the distal facing ledge 62 on lead screw 58 (see FIG. 13) when the dose setting mechanism is in the non-activated state and the dose button 86 is locked in the retracted or proximal-most position. As the outer sleeve 400 is rotated to a zero dose or initial position (i.e., where the the indicia arrow shown in FIG. 18 is moved to be visible in window 210 (see FIGS. 9-10) the inner sleeve 410 and key 412 are simultaneously rotated, which moves the stop face 413 from abutment with ledge 62 thus allowing spring 48 to move the lead screw 58 distally to the activated position where the dose button is popped out in the distal direction rearwardly relative to the housing 12a and the dose setting knob 84. Key 412 also has a chamfer 411 (see FIG. 19) that faces distally and is configured with a sloping or camming surface that will operatively engage with a proximal projecting end face 417 (see FIG. 14) in manner where axial movement of the lead screw 58 in the proximal direction, when the dose button is pushed to deliver a set dose of medicament, causes the inner sleeve 410 and key 412 to rotate against a biasing force of biasing element 420, as described in more detail below.

Key 412 is configured and designed to travel within a locking slot 430 during rotational movement caused by both the rotation of outer sleeve 400 and the engagement with end face 417 of the lead screw 58. Inner sleeve 410 is axially fixed relative to housing 12a and also has a connector 418, shown as a hole 418, or indentation, that fixedly attaches a proximal end of the biasing element 420. Biasing element 420 is illustrated in the embodiment in FIGS. 18 and 19 as a spring with opposing anchor posts 424 and 422. Connector 418 is configured to accept and retain post 424 to prevent rotational movement of spring 420. Post 422 is configured to attach to a similar connector 432 located in locking member 96a. Because locking member 96a is rotationally fixed to the outer housing 12a of the dose setting mechanism, the biasing element 420 exerts a rotational spring force on inner sleeve 410 such that the key 412 is biased in the locking position within the transverse portion 430b of locking slot 430. Locking member 96a also has stops 435, 436, and 437. The stops work collectively as a device to limit the rotation of the radially projecting rib 404 to certain degrees of rotation. The degree of rotation depends on the spacing between the neighboring two stops and can be adjusted according to design needs.

The interaction of the key 412 with the locking slot 430 will now be described. In the non-activated state of the dose setting mechanism the key 412 is positioned within the transverse portion 430b of the locking member 96a, which itself is axially fixed relative to the dose member assembly 66a and housing 12a. In this position the lead screw is blocked by the key 412 from moving axially in the distal direction. The indicia on the outer sleeve 400 will display a dose number (as opposed to the arrow or a "0") in the window of the housing. To activate the dose setting mechanism, a user will rotate the dose setting knob to an initial or start position in order to display the arrow or a "0". This rotational force overcomes the rotational biasing force exerted by biasing member 420 on the inner sleeve 410. Biasing element 420 exerts a biasing spring force to maintain key 412 against end wall 430c of the transverse portion 430b. Rotation of the outer sleeve causes the key 412 to rotate against the biasing spring force causing the key 412 to travel in the transverse portion 430b of locking lot 430 disengaging the key 412 from the ledge 62 of the lead screw 58. Spring 48 expands and pushes the lead screw 58 axially in the distal direction relative to the locking member 96a and the dose member assembly 66a. The lead screw 58 has now moved distally relative the key 412 such that the end face 417 of the lead screw 58 is positioned distally from the chamfer 411. This movement of the lead screw 58 causes the dose button to pop out of the distal end of the housing 12a relative to the dose setting knob placing the device in an activated state. At this point the dose setting knob can be rotated to set a fixed predetermined dose medicament, which also causes rotation of the lead screw relative to plunger rod 36. This rotation of the dose setting knob also rotates the outer and inner sleeves 400, 410 and returns the key 412 to abutment with end wall 430c of the locking slot 430. This rotation further causes end face 417 to align axially with chamfer 411. The device is now ready to deliver a dose.

To deliver the set dose the user pushes the dose button in the proximal direction causing the lead screw to move with it axially, thus engaging end face 417 with chamfer 411 causing rotation of the inner sleeve 410 to move key 412 away from end wall 430c against the biasing force of biasing element 420. As the axial rib 217 of the lead screw 58 moves past the key 412 it holds inner sleeve 410 from rotating back in response to the biasing force exerted by biasing element 420. Once the rib 217 moves proximally out of engagement with key 412 the inner sleeve 410 is then free to rotate back to end wall 430c in response to the biasing force of biasing element 420. At the end of the proximal travel of the lead screw the set dose of medicament has now been delivered. As a result of the resetting of the key 412 to abut end wall 430c, the device is now locked or in a non-activated state with the last set dose number shown in the housing window. To set another or subsequent dose, the user repeats the process of first unlocking the key from engagement with the leadscrew and then rotating the dose setting knob to set a dose.

It is to be understood that the embodiment described above and shown in the drawings is to be regarded only as a non-limiting example of the invention and that it may be modified in many ways within the scope of the patent claims.

The invention claimed is:

1. A dose setting mechanism for a medicament delivery device comprising,
    a housing having a longitudinal axis;
    a lead screw positioned with the housing;
    a locking member rotationally and slidably fixed to the housing, the locking member comprising a locking slot;
    a dose member assembly comprising a biasing element, an inner sleeve and an outer sleeve, where the dose member assembly is arranged coaxially around the locking member and the lead screw, the biasing element is operatively engaged with the locking member and the inner sleeve, and where the inner sleeve has a radially projecting key configured to travel in the locking slot to engage the lead screw to prevent axial movement of the lead screw when the dose setting mechanism is in a non-activated state.

2. The dose setting mechanism of claim 1 where the biasing element is a spring that exerts a rotational force on the inner sleeve.

3. The dose setting mechanism of claim 1 where the key disengages from the leadscrew when the dose setting member transitions from the non-activated state to an activated state.

4. The dose setting mechanism of claim 1 where the key comprises a chamfer projecting distally and configured to engage a proximal edge of an axial rib positioned on an outer surface the lead screw such that axial movement of the lead screw in a proximal direction causes rotation of the inner sleeve.

5. The dose setting mechanism of claim 1 where the inner sleeve further comprises an outer surface having a radially projecting protrusion.

6. The dose setting mechanism of claim 5 where the outer sleeve has a radially projecting rib located on an inner surface that is configured to engage the protrusion on the outer surface of the inner sleeve such that rotation of the outer sleeve causes rotation of the inner sleeve.

7. The dose setting mechanism of claim 1 where the locking slot is L-shaped.

8. The dose setting mechanism of claim 1 further comprising:
    a plunger rod rotationally fixed and axially slidable relative to the lead screw;
    a nut threadedly connected to the plunger rod rotationally fixed to the housing and axially slidable within a groove located at a proximal end of the lead screw; and
    a dose knob rotationally fixed to the outer sleeve of the dose member assembly and axially fixed to the housing, where a distal end portion of the outer sleeve of the dose member assembly slidably engages longitudinal ribs on an outer surface of the lead screw when the dose setting mechanism is in the activated state to rotationally fix the lead screw to the dose member.

9. The dose setting mechanism of claim 8 where the key is disengaged from the lead screw when the dose knob and the outer sleeve of the dose member assembly are rotated together with respect to the lead screw to a zero dose position.

10. The dose setting mechanism of claim 8 where the plunger rod has a non-circular cross-section.

11. The dose setting mechanism of claim 10 where a proximal through hole in the lead screw has a shape that corresponds and accepts the non-circular cross-section of the plunger rod such that the plunger is rotationally fixed and axially slidable relative to the lead screw.

12. The dose setting mechanism of claim 8 where a biasing force on the nut, plunger rod and lead screw in a distal direction results from a pre-tensioned compression spring positioned between a proximal end face of the nut and housing flange when the dose setting mechanism is in the non-activated state.

13. The dose setting mechanism of claim 8 further characterized in that the lead screw has proximally projecting ratchet teeth arranged radially around a proximal end of the lead screw, where the proximally projecting ratchet engage one or more cooperating distally projecting teeth on the nut such that during dose setting an audible sound is generated during dose setting.

14. The dose setting mechanism of claim 13 where each audible sound is directly proportional to each unit dose set.

15. The dose setting mechanism of claim 8 further characterized in that the nut comprises one or more proximally facing fingers that engage the groove such that axial movement of lead screw during transition from the non-activated state to the activated state causes axial movement of the nut in the same direction.

16. The dose setting mechanism of claim 1 further characterized in that a distal end face of the locking member comprises a zero dose stop that engages a corresponding stop on the dose member assembly when the dose setting mechanism transitions from the non-activated state to an activated state.

17. The dose setting mechanism of claim 1 where the outer sleeve and the inner sleeve of the dose member assembly have a circular cross-section.

18. The dose setting mechanism of claim 1 further characterized in that the outer sleeve of the dose member assembly comprises an outer surface having indicia indicative of a set dose.

19. The dose setting mechanism of claim 18 where the housing further comprises a dose window that is configured to allow viewing of the indicia.

* * * * *